(12) United States Patent
Ryan et al.

(10) Patent No.: US 9,889,286 B2
(45) Date of Patent: Feb. 13, 2018

(54) FIDUCIAL DEPLOYMENT MECHANISMS, AND RELATED METHODS OF USE

(71) Applicant: Boston Scientific Scimed, Inc., Maple Grove, MN (US)

(72) Inventors: Shawn Ryan, Upton, MA (US); Joseph A. Levendusky, Groton, MA (US); Robert B. DeVries, Northboro, MA (US); William Cole Lafferty, Natick, MA (US); Andrew Kendall Hollett, Somerville, MA (US); Brian Intoccia, Denver, CO (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 848 days.

(21) Appl. No.: 14/298,099

(22) Filed: Jun. 6, 2014

(65) Prior Publication Data

US 2014/0371586 A1 Dec. 18, 2014

Related U.S. Application Data

(60) Provisional application No. 61/834,235, filed on Jun. 12, 2013.

(51) Int. Cl.
*A61B 5/05* (2006.01)
*A61M 37/00* (2006.01)
(Continued)

(52) U.S. Cl.
CPC ......... *A61M 37/0069* (2013.01); *A61B 90/39* (2016.02); *A61B 10/0283* (2013.01);
(Continued)

(58) Field of Classification Search
CPC ............... A61M 37/0069; A61B 90/39; A61B 2090/3966; A61B 2090/3925; A61B 2090/3987; A61B 10/0283
(Continued)

(56) References Cited

U.S. PATENT DOCUMENTS 9,072,542 B2 * 7/2015 Ducharme ......... A61B 17/3468
9,522,264 B2 * 12/2016 Clancy .............. A61M 37/0069
(Continued)

FOREIGN PATENT DOCUMENTS

| EP | 2540241 A2 | 1/2013 |
|---|---|---|
| WO | WO 2012/033760 A1 | 3/2012 |
| WO | WO 2013/055568 A1 | 4/2013 |

OTHER PUBLICATIONS

International Search Report and Written Opinion corresponding to International Application No. PCT/US2014/041278, dated Dec. 2, 2014 (18 pages).

*Primary Examiner* — Sanjay Cattungal
(74) *Attorney, Agent, or Firm* — Bookoff McAndrews, PLLC

(57) ABSTRACT

A medical device that may include an elongate member having a proximal end and a distal end, and a lumen disposed through the elongate member is disclosed. The medical device may also include an opening disposed at the distal end of the elongate member in communication with the lumen, and a pushing element disposed with the lumen. The medical device may also include at least one fiducial disposed within the lumen and distal to the pushing element, and a separating mechanism disposed at the distal end of the elongate member. The separating mechanism may be configured to apply a separating force to deploy the at least one fiducial.

14 Claims, 8 Drawing Sheets

(51) Int. Cl.
*A61B 90/00* (2016.01)
*A61B 10/02* (2006.01)

(52) U.S. Cl.
CPC ............... *A61B 2090/3925* (2016.02); *A61B 2090/3966* (2016.02); *A61B 2090/3987* (2016.02)

(58) Field of Classification Search
USPC ................................................ 600/407–480
See application file for complete search history.

(56) References Cited

U.S. PATENT DOCUMENTS

2003/0233101 A1\* 12/2003 Lubock ............. A61M 37/0069
606/116
2013/0006101 A1\* 1/2013 McHugo ............ A61B 17/3468
600/424

\* cited by examiner

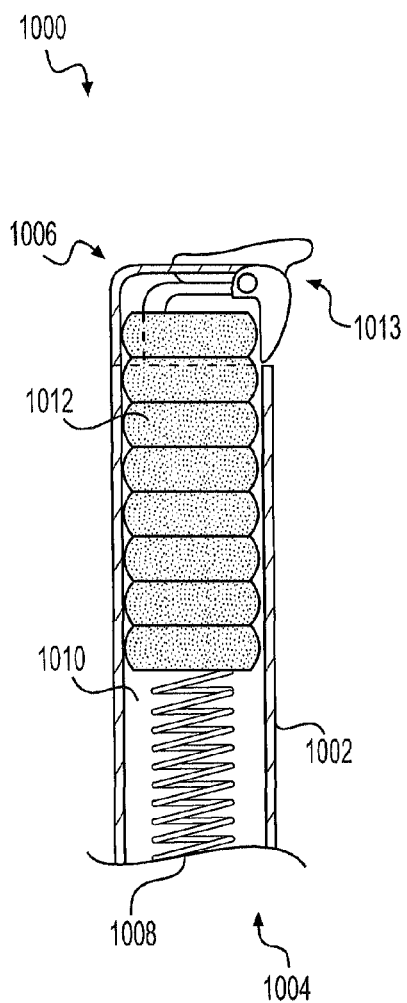 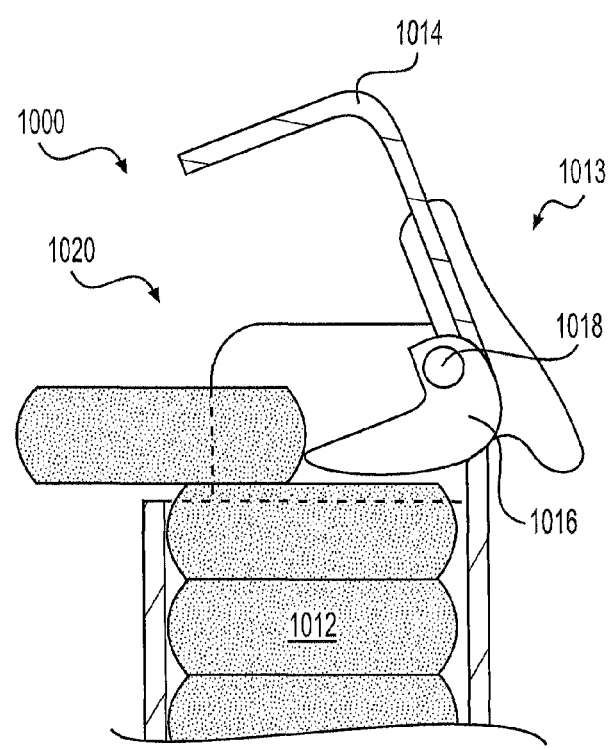
FIG. 10      FIG. 11

FIDUCIAL DEPLOYMENT MECHANISMS, AND RELATED METHODS OF USE

CROSS-REFERENCE TO RELATED APPLICATIONS

This application claims the benefit of priority of U.S. Provisional Application No. 61/834,235, filed Jun. 12, 2013, the entirety of which is incorporated by reference herein.

TECHNICAL FIELD

Various embodiments of the present disclosure relate generally to medical devices and related systems and methods. More specifically, the present disclosure relates to devices, systems, and methods for deploying fiducials.

BACKGROUND

Endosonographers use Endoscopic Ultrasound Fine Needle Aspiration (EUS FNA) for diagnosis and staging of disease. EUS FNA is a highly effective diagnostic procedure. An ultrasound image generated by EUS FNA allows a physician to visualize the position of a needle in relation to a target and surrounding tissue structures. This aids in ensuring that the correct tissue is sampled and that the risk to the patient is minimized.

However, therapeutic tools and procedures for endosonographers are less well established. Current industry trends and research are focusing on development of devices that would enable endosonographers to treat specific conditions once diagnosis has been established.

One area currently being explored for EUS guided therapy is the placement of fiducials. Fiducials act as markers so diseased tissue can be targeted for more effective delivery of radiation or other treatments. Currently, the fiducial placement is a very time consuming procedure for the endosonographers. It generally requires the physician to load and place the markers one at a time.

SUMMARY

The present disclosure includes devices, systems, and methods for deploying fiducials, for example, during an EUS FNA procedure.

In accordance with an embodiment, the present disclosure is directed to a medical device. The medical device may include an elongate member having a proximal end and a distal end, and a lumen disposed through the elongate member. The medical device may also include an opening disposed at the distal end of the elongate member in communication with the lumen, and a pushing element disposed with the lumen. The medical device may also include at least one fiducial disposed within the lumen and distal to the pushing element, and a separating mechanism disposed at the distal end of the elongate member. The separating mechanism may be configured to apply a separating force to deploy the at least one fiducial.

Various embodiments of the disclosure may include one or more of the following aspects: wherein the at least one fiducial may be one of a plurality of fiducials disposed within the lumen and connected to each other by a linkage; wherein the separating mechanism may be configured to direct the separating force to a distal portion of the linkage to deploy a distalmost fiducial; wherein the at least one fiducial may be one of a plurality of fiducials disposed within the lumen, and adjacent fiducials may be disposed within compartments separated by spacers; and wherein the separating mechanism may be configured to apply the separating force to a distalmost spacer to deploy a distalmost fiducial.

In accordance with an embodiment, the present disclosure is directed to a method of deploying multiple fiducials within a patient. The method may include advancing a medical device into a body lumen of the patient, and applying a distally-directed force to direct at least one fiducial toward an opening at a distal end of the medical device. The method may also include applying a separating force, distinct from the distally-directed force, to deploy the fiducial.

Various embodiments of the disclosure may include one or more of the following aspects: wherein the distally-directed force may be applied by a pushing element disposed within a lumen of the medical device; wherein the separating force may be one of an electric charge, heat, or a mechanical force; wherein the at least one fiducial may be one of a plurality of fiducials connected to each other by a linkage, and the method may further include applying the separating force to a distal portion of the linkage to deploy a distal fiducial; wherein the at least one fiducial may be one of a plurality of fiducials disposed within the lumen, and adjacent fiducials may be disposed within compartments separated by spacers, and the method may further include applying the separating force to a distalmost spacer to deploy a distalmost fiducial; and applying the separating force to a distal end of a continuous length of fiducial material to form a plurality of fiducials.

In accordance with an embodiment, the present disclosure is directed toward a medical device. The medical device may include an elongate member having a proximal end and a distal end, and a first lumen disposed through the elongate member. The method device may also include an opening disposed at the distal end of the elongate member in communication with the lumen, and a plurality of fiducials disposed within the first lumen. The medical device may also include at least one biasing element disposed within the first lumen proximal to the plurality of fiducials. The biasing element may be configured to urge the plurality of fiducials toward the opening after deployment of a distalmost fiducial.

Various embodiments of the disclosure may include one or more of the following aspects: a distal opening mechanism disposed at the distal end of the elongate member, the distal opening mechanism configured to rotate about a joint to eject a distalmost fiducial from the first lumen; and a second lumen may be disposed in the elongate member parallel to the first lumen, and a pushing element may be disposed through the second lumen, the pushing element being configured to reciprocally move between a proximal loading position and a distal deployment position, wherein when the pushing element is in the proximal loading position and no fiducial is in the second lumen, a distalmost fiducial disposed within the first lumen is urged toward the second lumen.

In accordance with an embodiment, the present disclosure is directed toward a medical device. The medical device may include an elongate member having a proximal end and a distal end, and a lumen disposed through the elongate member. The medical device may also include an opening disposed at the distal end of the elongate member in communication with the lumen, and a plurality of fiducials disposed distal to the pushing element. The medical device may also include a pull wire having a distal protrusion being disposed distal to a distalmost fiducial of the plurality of fiducials and configured to retain the plurality of fiducials within the lumen.

In accordance with an embodiment, the present disclosure is directed toward a medical device. The medical device may include an elongate member having a proximal end and a distal end, and a lumen disposed through the elongate member. The medical device may also include an opening disposed at the distal end of the elongate member in communication with the lumen, and a plurality of fiducials disposed distal to the pushing element, each of the plurality of fiducials having a protrusion. The medical device may also include a groove disposed on a side surface of the elongate member that receives the protrusion of each of the plurality of fiducials.

In accordance with an embodiment, the present disclosure is directed toward a medical device. The medical device may include an elongate member having a proximal end and a distal end, and a lumen disposed through the elongate member. The medical device may also include an opening disposed at the distal end of the elongate member in communication with the lumen, and a plurality of fiducials disposed within the lumen. The medical device may also include a pushing element configured to direct the plurality of fiducials through the opening, and a liquid disposed between adjacent fiducials.

In accordance with an embodiment, the present disclosure is directed toward a medical device. The medical device may include an elongate member having a proximal end and a distal end, and a lumen disposed through the elongate member. The medical device may also include an opening disposed at the distal end of the elongate member in communication with the lumen, and a cartridge disposed at the distal end of the elongate member distal to the pushing element. The cartridge may have a plurality of chambers disposed radially about the cartridge. The medical device may also include a plurality of fiducials disposed within the plurality of chambers.

In accordance with an embodiment, the present disclosure is directed toward a medical device. The medical device may include an elongate member having a proximal end and a distal end, and a lumen disposed through the elongate member. The medical device may also include an opening disposed at the distal end of the elongate member in communication with the lumen, and a plurality of fiducials disposed within the lumen. The medical device may also include an actuator disposed at a proximal end of the elongate member. The actuator may include a cap having a distal projection. The medical device may also include a plurality of seats configured to couple with the distal projection. Adjacent seats of the plurality of seats may be transposed about the longitudinal axis of the elongate member, and the longitudinal distance between adjacent seats may correspond to the longitudinal distance moved by the actuator to deploy a single fiducial of the plurality of fiducials.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

FIGS. 10-11 are partial side cross-sectional views of a deployment mechanism in accordance with an embodiment of the present disclosure.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts.

Figure 1:
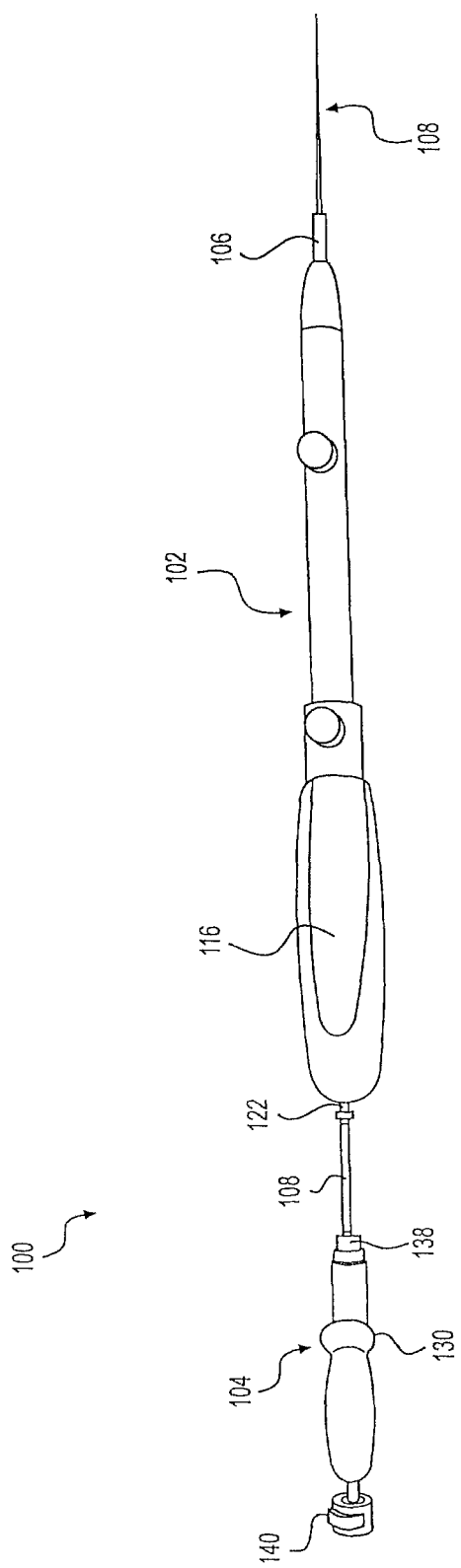
FIG. 1 is a side perspective view of a medical device in accordance with an embodiment of the present disclosure.

As shown in FIG. 1, a medical device 100 according to an exemplary embodiment of the present disclosure may include a first needle 102 and a second needle 104 connectable to one another. A further example of a suitable medical device includes that described in U.S. Patent Application Publication 2011/0196258, published on Aug. 11, 2011, the entire disclosure of which is incorporated by reference herein. First needle 102 may include a first longitudinal element 106 defining a lumen (not shown). First longitudinal element 106 may be flexible such that first longitudinal element 106 may be inserted into the body along a tortuous path (e.g., within a body lumen) to reach a target area within the body.

A proximal end of first longitudinal element 106 may be coupled to a first handle 116 sized to slidably receive first longitudinal element 106. First handle 116 may further include a luer fitting 122 for coupling to the second needle 104. Second longitudinal element 108 may extend longitudinally from a proximal end to a distal end and include a lumen (not shown). An outer diameter of second longitudinal element 108 may be smaller than an inner diameter of the first lumen of first longitudinal element 106 such that second longitudinal element 108 may be slidably inserted through the first lumen. For example, in one embodiment, first longitudinal element 106 may be a 19 gauge needle while second longitudinal element 108 may be a 22 gauge needle. Alternatively, first longitudinal element 106 may be a 22 gauge needle while second longitudinal element 108 may be a 25 gauge needle.

A length of second longitudinal element 108 may be longer than a length of first longitudinal element 106 such that when the second longitudinal element 108 is inserted into the first lumen, the distal end of the second longitudinal element 108 may be extended distally past the distal end of the first longitudinal element 106. The proximal end of the second longitudinal element 108 may include an actuator 140.

A second handle 130 may be attached to the proximal end of second longitudinal element 108. The distal end of the second handle 130 may include a coupling element 138 adapted and configured to mate with the luer fitting 122 of first needle 102 such that first and second needles 102, 104 may be connected to one another.

Second longitudinal element 108 of second needle 104 may be inserted through the lumen of first longitudinal element 106 of first needle 102 such that second longitudinal element 108 is "nested" within first longitudinal element 106. Second longitudinal element 108 may be slid through the lumen of first longitudinal element 106 until coupling element 138 of second needle 104 comes into contact with luer fitting 122 of first needle 102.

Figure 2:
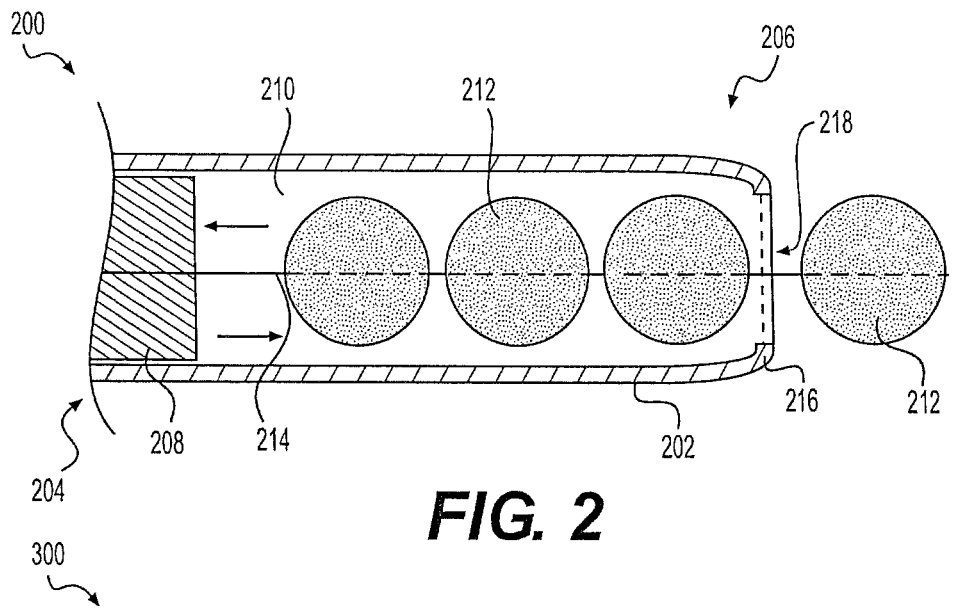
FIGS. 2-6 are partial side cross-sectional views of deployment mechanisms in accordance with various embodiments of the present disclosure.

FIG. 2 shows a partial side cross-sectional view of a medical device 200 for deploying fiducials in accordance with an embodiment of the present disclosure. Medical device 200 may include an elongate member 202 having a proximal end 204 and a distal end 206. The elongate member 202 may be inserted into a lumen of a patient's body to access a target site whereupon a medical or diagnostic procedure, such as EUS FNA, is performed. The proximal end 204 may be coupled to an actuating mechanism, such as actuator 140 (referring to FIG. 1), for operating the medical device 200. In some embodiments, medical device 200 may represent the distal end of second longitudinal element 108 (referring to FIG. 1).

A pushing element 208 may be disposed within a lumen 210 defined by elongate member 202. Pushing element 208 may be coupled to actuator 140 in any suitable manner. Pushing element 208 may be advanced distally by actuator 140 and may contact a fiducial 212 disposed within lumen 210. A plurality of fiducials 212 may be disposed along a longitudinal axis of lumen 210 and may be connected to each other by a linkage 214. Linkage 214 may extend within and between the plurality of fiducials 212. Linkage 214 may be a wire, suture, or other suitable linkage. Fiducials 212 may include a generally radiopaque material so that targeted regions of a patient's body may be located by ultrasound or other suitable imaging techniques. Fiducials 212 may likewise include a porous, pitted, angled, rough, or irregular surface in order to improve visibility under ultrasound or other suitable imaging techniques, including by providing structures on the surface(s) of the fiducial 212. Fiducials 212 may include gold or another suitable metal. In some embodiments, fiducials 212 may further include compliant materials. In one embodiment, fiducials 212 may be spherical, although any other suitable shape also may be utilized, including shapes selected to improve visibility under ultrasound, e.g. polygonal. In an alternative embodiment, fiducials 212 may include substance-eluting (e.g., drug-eluting) materials. Fiducials 212 may likewise be configured for placement at a desired region of a patient's body, including by implantation on, within, or underneath tissue at a targeted region of a patient's body by piercing, cutting, or separating tissue at the desired region, or by adhering the fiducial 212 to the tissue by, e.g., providing an adhesive coating or pattern on the surface of fiducial 212.

A separating mechanism 216 may be disposed at distal end 206 of medical device 200. Separating mechanism 216 may be configured to disintegrate or otherwise sever linkage 214 between consecutive fiducials 212. In one exemplary embodiment, as pushing element 208 is moved distally (e.g., by actuator 140), a distalmost fiducial 212 may extend distally out of lumen 210 via an opening 218. In an alternative embodiment, elongate member 202 may be moved proximally (while pushing member 208 is held in place) to eject the distalmost fiducial 212 out of lumen 210. In yet another alternative embodiment, pushing element 208 may be coupled to linkage 214, and both pushing element 208 and linkage 214 may be moved proximally such that a distalmost end of linkage 214 is removed from the distalmost fiducial 212, releasing the distalmost fiducial 212.

In one embodiment, once a distalmost linkage 214 is within an effective range of separating mechanism 216, separating mechanism 216 may generate a separating force to deploy a distalmost fiducial 212. In one embodiment, separating mechanism 216 may emit an electrical charge that disintegrates or severs a distalmost portion of linkage 214. Current carrying wires (not shown) may extend through medical device 200 to proximal end 204, where they may be coupled to, e.g., an RF generator or other suitable mechanism. An actuator (not shown) may be disposed at proximal end 204 that may be activated to cause current to flow along the current carrying wires and across opening 218 to separate fiducials 212. In an alternative embodiment, separating mechanism 216 may direct heat toward linkage 214, thereby melting linkage 214 and releasing the distalmost fiducial 212. It should be noted, however, that other alternative separating mechanisms utilizing electrical, mechanical, and/or chemical mechanism are also contemplated.

Figure 3:
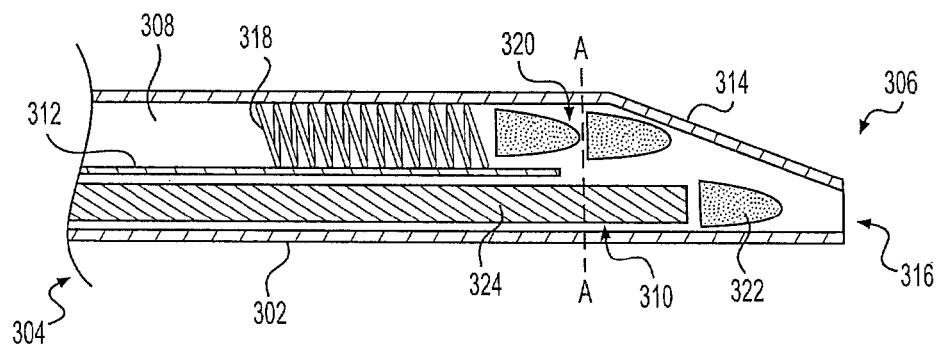

FIG. 3 is a partial side cross-sectional view of a deployment mechanism in accordance with an embodiment of the present disclosure. A medical device 300 may include an elongate member 302 having a proximal end 304 and a distal end 306. Similar to elongate member 202, elongate member 302 may be inserted into a lumen of a patient's body to access a target site whereupon a medical or diagnostic procedure, such as EUS FNA, is performed. The proximal end 304 may be coupled to an actuating mechanism, such as actuator 140 (referring to FIG. 1), for operating the medical device 300. In some embodiments, medical device 300 may represent the distal end of second longitudinal element 108 (referring to FIG. 1).

Elongate member 302 may be a needle defined by a first lumen 308 and a second lumen 310 that are parallel to each other and separated by a wall 312. Elongate member 302 may include a tapered section 314 disposed partway around the circumference of elongate member 302 that extends from an intermediate portion of elongate member 302 toward an opening 316 disposed at distal end 306. A biasing element 318 may be disposed in first lumen 308 and may be located proximally to a loading zone 320 configured to hold a plurality of fiducials 322. Loading zone 320 may thus be defined by biasing element 318, wall 312, tapered section 314, and an inner portion of elongate member 302. In one embodiment, biasing element 318 may be a coiled spring. Alternatively, biasing element 318 may be any suitable structure capable of providing a biasing force including, but not limited to, other compressible materials.

A pushing element 324 may be disposed within second lumen 310 and may be capable of reciprocal movement to load and eject fiducials 322 one at a time from elongate member 302. As shown in FIG. 3, pushing element 324 may be in an intermediate position, where a fiducial 322 is in a loaded position distal to the distal end of pushing element 324. Pushing element 324 may be moved distally toward opening 316 to eject a loaded fiducial out of elongate member 302. In a fully extended position, the distal end of pushing element 324 may be coplanar with opening 316 or proximal to opening 316. Alternatively, the distal end of pushing element 324 may extend through opening 316 to deploy fiducials 322. After deployment of a fiducial 322, pushing element 324 may be retracted to a loading position represented by reference axis A-A (i.e., a location that is proximal to a distalmost fiducial 322 within first lumen 308). That is, pushing element 324 may be retracted so that its distal end is located generally along axis A-A, and a distal-most fiducial 322 located in loading zone 320 may be laterally urged by biasing element 318 and tapered section 314 toward second lumen 310 and the distal end of pushing element 324. After loading of a fiducial 322, pushing element 324 may be returned to the intermediate position.

Figure 4:
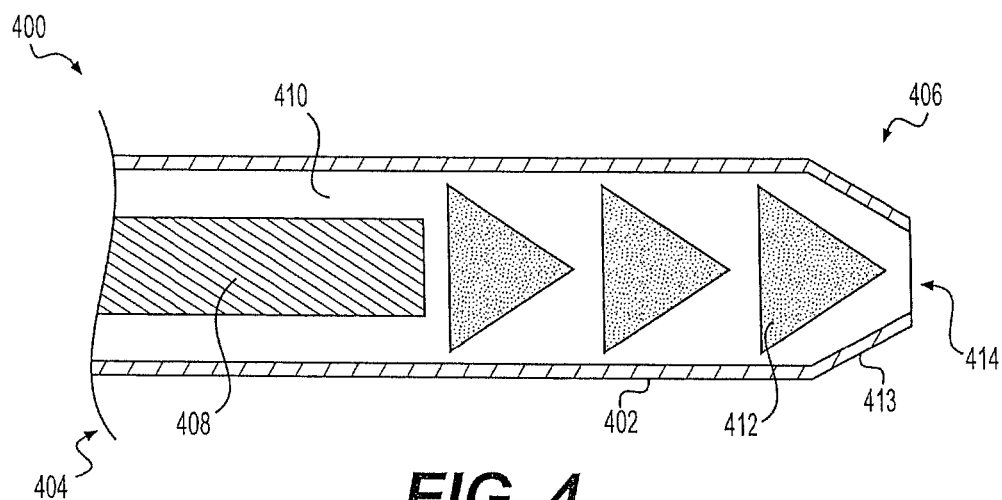

FIG. 4 is a partial side cross-sectional view of a deployment mechanism in accordance with an embodiment of the present disclosure. A medical device 400 may include an elongate member 402 having a proximal end 404 and a distal end 406. Similar to elongate member 202, elongate member 402 may be inserted into a lumen of a patient's body to access a target site whereupon a medical or diagnostic procedure, such as EUS FNA, is performed. The proximal end 404 may be coupled to an actuating mechanism, such as actuator 140 (referring to FIG. 2), for operating the medical device 400. In some embodiments, medical device 400 may represent the distal end of second longitudinal element 108 (referring to FIG. 1).

A pushing element 408 may be disposed within a lumen 410 defined by elongate member 402. Pushing element 408 may be coupled to actuator 140 in any suitable manner. Pushing element 408 may be advanced distally by actuator 140 and may contact a fiducial 412 disposed within lumen 410. A plurality of fiducials 412 may be disposed along a longitudinal axis of lumen 410. Fiducials 412 may be substantially similar to fiducials 212 (referring to FIG. 2), but may be shaped such that fiducials 412 are retained in lumen 410 absent a compressing force applied to them. In one embodiment, at least one diameter of fiducials 412 is greater than the diameters of both a tapered section 413 and an opening 414 disposed at distal end 406 of elongate member 402. Fiducials 412 may be conical, though any other suitable shape is also contemplated including, but not limited to spherical, ovular, rectangular, asymmetrical, or the like. Tapered section 413 may be an interference fit taper section that extends entirely around a circumference of elongate member 402 that defines opening 414. In an alternative embodiment, instead of having a smaller diameter than a remaining portion of elongate member 402, tapered section 413 may have substantially the same diameter as the remaining portion of elongate member 402 but also include inward protrusions that reduce an effective diameter of lumen 410 at tapered section 413. Fiducials 412 may include a compliant material such that fiducials 412 are contained within lumen 410. That is, a compressing force may be applied to fiducials 412, reducing the effective diameter of fiducials 412 to enable them to eject from elongate member 402 via tapered section 413 and opening 414 (i.e., fiducials 412 may snap through tapered section 413 and opening 414 when a sufficient compressive and distally-directed force is applied). In an alternative embodiment, elongate member 402 may be moved proximally (while pushing member 408 is held in place) to apply the compressing force to a distalmost fiducial 412, enabling it to eject out of lumen 410.

Figure 5:
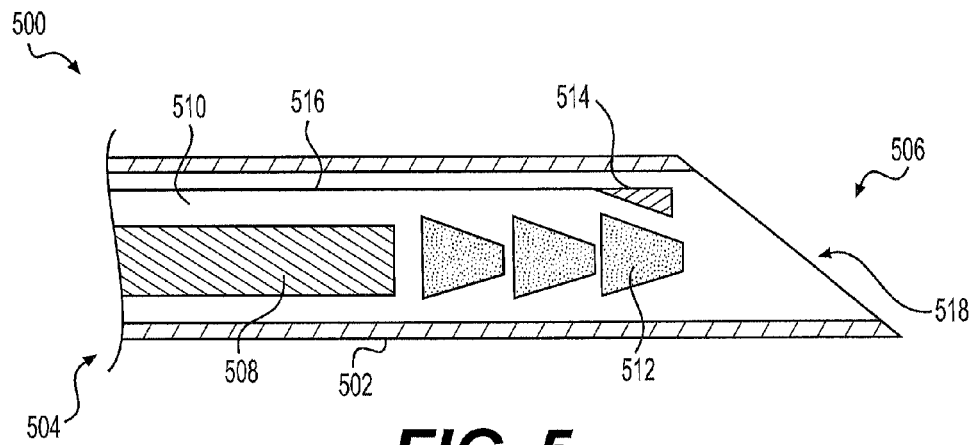

FIG. 5 is a partial side cross-sectional view of a deployment mechanism in accordance with an embodiment of the present disclosure. A medical device 500 may include an elongate member 502 having a proximal end 504 and a distal end 506. Similar to elongate member 202, elongate member 502 may be inserted into a lumen of a patient's body to access a target site whereupon a medical or diagnostic procedure, such as EUS FNA, is performed. The proximal end 504 may be coupled to an actuating mechanism, such as actuator 140 (referring to FIG. 1), for operating the medical device 500. In some embodiments, medical device 500 may represent the distal end of second longitudinal element 108 (referring to FIG. 1).

A pushing element 508 may be disposed within a lumen 510 defined by elongate member 502. Pushing element 508 may be coupled to actuator 140 in any suitable manner. Pushing element 508 may be advanced distally by actuator 140 and may contact a fiducial 512 disposed within lumen 510. A plurality of fiducials 512 may be disposed along a longitudinal axis of lumen 510. Fiducials 512 may be substantially similar to fiducials 412 (referring to FIG. 4), but may be shaped such that fiducials 512 are contained by a projection 514 extending from a pull wire 516 disposed within lumen 510. Similar to pushing element 508, pull wire 516 may be coupled to actuator 140 or a similar mechanism. In one embodiment, fiducials 512 may be conical, though any other suitable shape is also contemplated including, but not limited to spherical, ovular, rectangular, asymmetrical, or the like. Fiducials 512 may include a compliant material and may be contained within lumen 510 by projection 514 unless a sufficient compressing force is applied. That is, projection 514 may be sized to inhibit the distal movement of fiducials 512. To deploy a distalmost fiducial 512, pull wire 516 may be retracted proximally so that projection 514 is proximal to the distalmost fiducial 512. Then, pushing element 508 may be directed distally to eject distalmost fiducial 512 out of lumen 510 via an opening 518. In an alternative embodiment, elongate member 502 may be moved proximally (while pushing member 508 is held in place) to eject the distalmost fiducial 512 out of lumen 510. It should also be noted that as projection 514 is moved proximal to the distalmost fiducial 512, projection 514 may secure (inhibit the distal movement of) a proximally adjacent fiducial 512 in place for a subsequent deployment.

Figure 6:
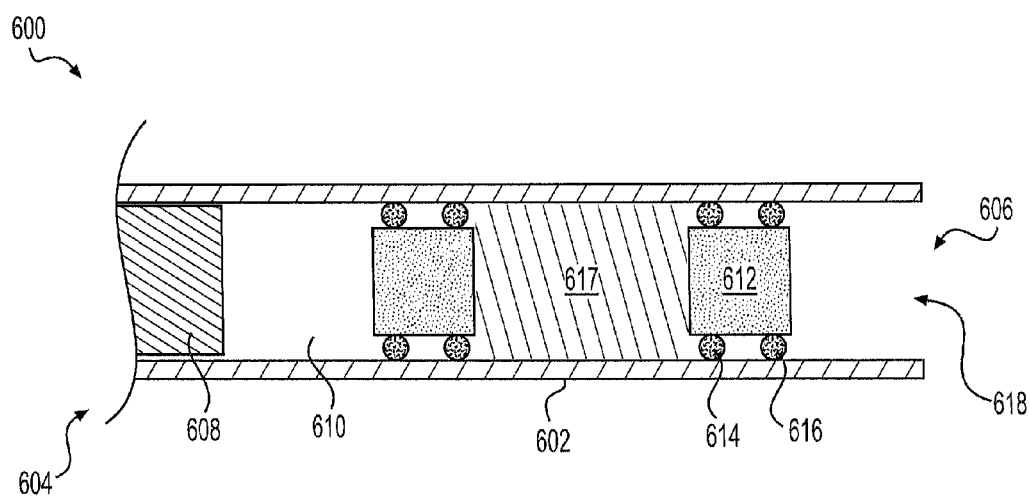

FIG. 6 is a partial side cross-sectional view of a deployment mechanism in accordance with an embodiment of the present disclosure. A medical device 600 may include an elongate member 602 having a proximal end 604 and a distal end 606. Similar to elongate member 202, elongate member 602 may be inserted into a lumen of a patient's body to access a target site whereupon a medical or diagnostic procedure, such as EUS FNA, is performed. The proximal end 604 may be coupled to an actuating mechanism, such as actuator 140 (referring to FIG. 1), for operating the medical device 600. In some embodiments, medical device 600 may represent the distal end of second longitudinal element 108 (referring to FIG. 1).

A pushing element 608 may be disposed within a lumen 610 defined by elongate member 602. Pushing element 608 may be coupled to actuator 140 in any suitable manner. Pushing element 608 may be advanced distally by actuator 140 and may contact a fiducial 612 disposed within lumen 610. A plurality of fiducials 612 may be disposed along a longitudinal axis of lumen 610. Fiducials 612 may be substantially similar to fiducials 212 (referring to FIG. 2), but also include a first seal 614 and a second seal 616. Both first seal 614 and second seal 616 may be disposed around a periphery of fiducials 612. Adjacent fiducials 612 may be separated by a liquid volume 617 (e.g., saline) to promote separation and ease of deployment. Further, the presence of liquid volume 617 between adjacent fiducials 612 may reduce the formation of air pockets within a patient's body during deployment of fiducials 612, improving the clarity of images generated by ultrasound and other imaging techniques. In one exemplary embodiment, as pushing element 608 is moved distally (e.g., by actuator 140 of FIG. 1), a distalmost fiducial 612 may extend distally out of lumen 610 via an opening 618. In an alternative embodiment, elongate member 602 may be moved proximally (while pushing member 608 is held in place) to eject a distalmost fiducial 612 out of lumen 610. First and second seals 614, 616 may be O-rings or similar structures, and may have material properties that permit them to "roll" along the inside of lumen 610 with its corresponding fiducial 612. Thus, as fiducials 612 are moved distally, liquid volume 617 may be maintained between adjacent fiducials 612.

Figure 7:
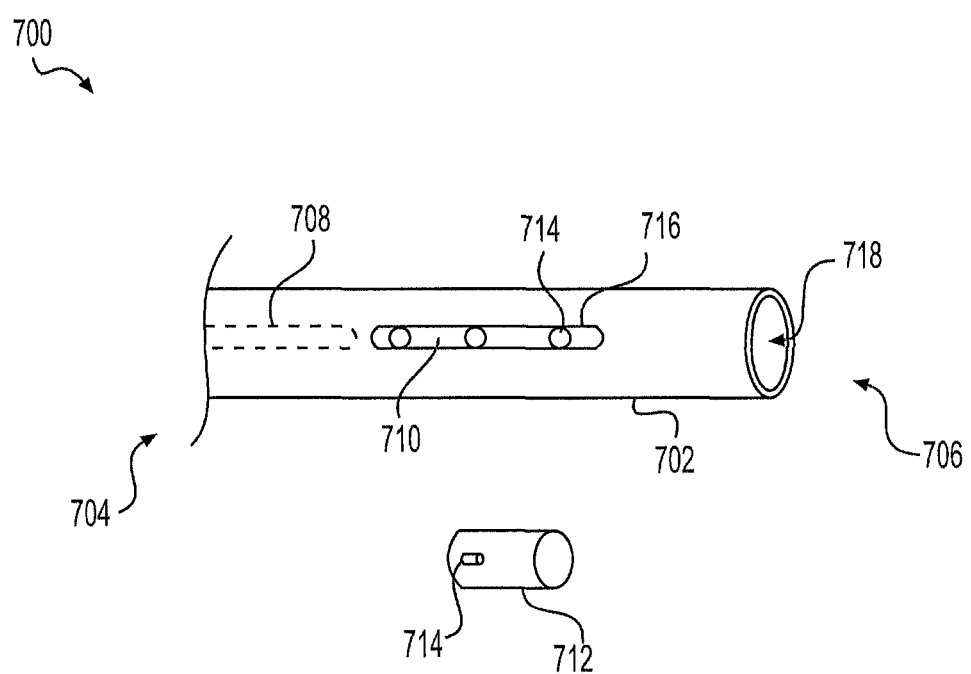
FIG. 7 is a side perspective view of a medical device in accordance with an embodiment of the present disclosure.

FIG. 7 is a partial side perspective view of a deployment mechanism in accordance with an embodiment of the present disclosure. A medical device 700 may include an elongate member 702 having a proximal end 704 and a distal end 706. Similar to elongate member 202, elongate member 702 may be inserted into a lumen of a patient's body to access a target site whereupon a medical or diagnostic procedure, such as EUS FNA, is performed. The proximal end 704 may be coupled to an actuating mechanism, such as actuator 140 (referring to FIG. 1), for operating the medical device 700. In some embodiments, medical device 700 may represent the distal end of second longitudinal element 108 (referring to FIG. 1).

A pushing element 708 may be disposed within a lumen 710 defined by elongate member 702. Pushing element 708 may be coupled to actuator 140 in any suitable manner. Pushing element 708 may be advanced distally by actuator 140 and may contact a fiducial 712 disposed within lumen 710. A plurality of fiducials 712 may be disposed along a longitudinal axis of lumen 710. Fiducials 712 may be substantially similar to fiducials 212 (referring to FIG. 2), but also include a protrusion 714 extending from a longitudinal surface of each fiducial 712. Protrusions 714 may be arranged within lumen 710 such that protrusions 714 are disposed within a groove 716 disposed within a longitudinal surface of elongate member 702. That is, as fiducials 712 move distally through lumen 710, protrusions 714 may promote proper orientation and deployment of fiducials 712 via its interaction with groove 716. Further, protrusions 714 may act as retention elements, preventing deployment of fiducials 712 unless a sufficient compressing and distally-directed force is applied by pushing element 708. Protrusions 714 and/or fiducials 712 may be compressible to facilitate deployment of fiducials 712. Groove 716 may extend from a first longitudinal point to a second longitudinal point along the longitudinal axis of elongate member 702, though other suitable configurations are also contemplated. For example, in one alternative embodiment, groove 716 may extend to proximal end 704 and/or distal end 706 of elongate member 702. In one exemplary embodiment, as pushing element 708 is moved distally (e.g., by actuator 140 of FIG. 1), a distalmost fiducial 712 may extend distally out of lumen 710 via an opening 718. In an alternative embodiment, elongate member 702 may be moved proximally (while pushing member 708 is held in place) to eject the distalmost fiducial 712 out of lumen 710. It is also contemplated that elongate member 702 may include a tapered section to retain fiducials 712 within lumen 710.

Figure 8:
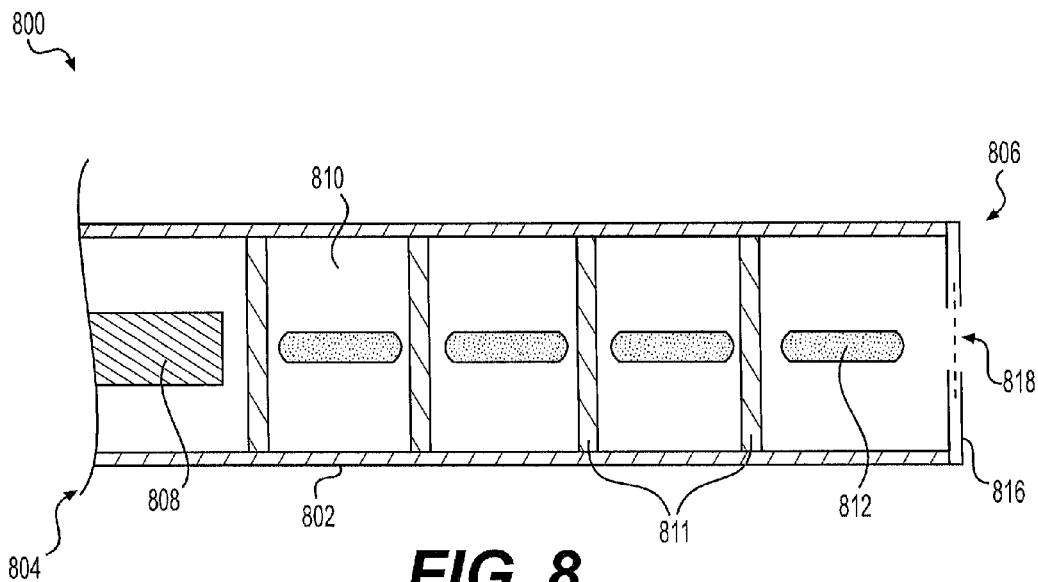
FIGS. 8-9 are partial side cross-sectional views of deployment mechanisms in accordance with various embodiments of the present disclosure.

FIG. 8 is a partial side cross-sectional view of a deployment mechanism in accordance with an embodiment of the present disclosure. A medical device 800 may include an elongate member 802 having a proximal end 804 and a distal end 806. Similar to elongate member 202, elongate member 802 may be inserted into a lumen of a patient's body to access a target site whereupon a medical or diagnostic procedure, such as EUS FNA, is performed. The proximal end 804 may be coupled to an actuating mechanism, such as actuator 140 (referring to FIG. 1), for operating the medical device 800. In some embodiments, medical device 800 may represent the distal end of second longitudinal element 108 (referring to FIG. 1).

A pushing element 808 may be disposed within a lumen 810 defined by elongate member 802. Pushing element 808 may be coupled to actuator 140 in any suitable manner. Pushing element 808 may be advanced distally by actuator 140 and may contact a spacer 811 disposed within lumen 810. A plurality of fiducials 812 may be disposed in compartments along a longitudinal axis of lumen 810 between adjacent spacers 811. Fiducials 812 may be substantially similar to fiducials 212 (referring to FIG. 2).

A separating mechanism 816 may be disposed at distal end 806 of medical device 800. Separating mechanism 816 may be substantially similar to separating mechanism 216 (referring to FIG. 2) and may be configured to disintegrate or otherwise sever spacers 811 between consecutive fiducials 812. In one exemplary embodiment, as pushing element 808 is moved distally (e.g., by actuator 140 of FIG. 1), a distalmost spacer 811 may extend distally toward an opening 818 disposed at distal end 806 of elongate member 802. In an alternative embodiment, elongate member 802 may be moved proximally (while pushing member 808 is held in place) to direct the distalmost spacer 811 toward distal end 806.

In one embodiment, once a distalmost spacer 811 is within an effective range of separating mechanism 816, separating mechanism 816 may generate a separating force to deploy a distalmost fiducial 812. In one embodiment, separating mechanism 816 may emit an electrical charge that severs spacer 811. In an alternative embodiment, separating mechanism 816 may direct heat toward spacer 811, thereby melting spacer 811 and releasing the distalmost fiducial 812. It should be noted, however, that other alternative separating mechanisms utilizing electrical, mechanical, and/or chemical mechanism are also contemplated.

Figure 9:
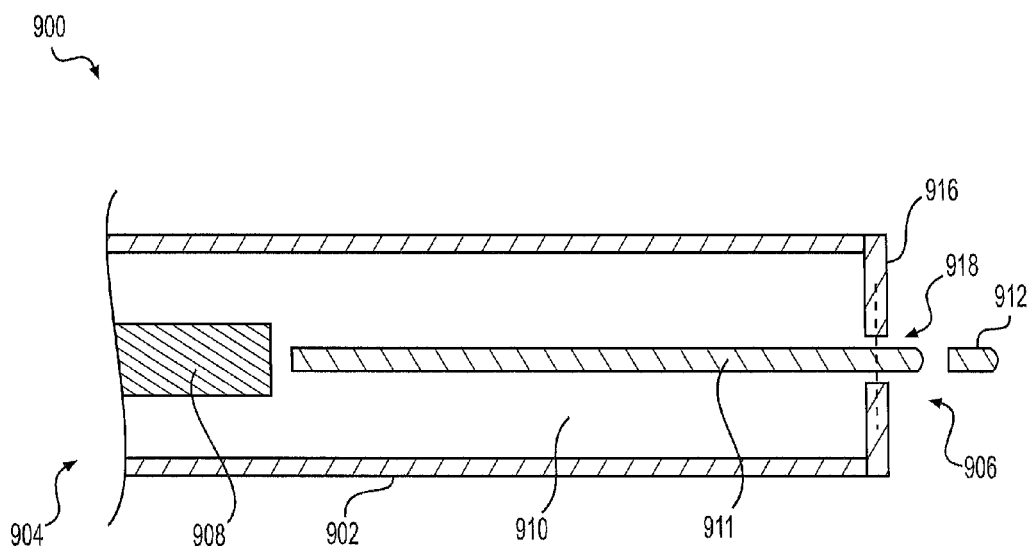

FIG. 9 is a partial side cross-sectional view of a deployment mechanism in accordance with an embodiment of the present disclosure. A medical device 900 may include an elongate member 902 having a proximal end 904 and a distal end 906. Similar to elongate member 202, elongate member 902 may be inserted into a lumen of a patient's body to access a target site whereupon a medical or diagnostic procedure, such as EUS FNA, is performed. The proximal end 904 may be coupled to an actuating mechanism, such as actuator 140 (referring to FIG. 1), for operating the medical device 900. In some embodiments, medical device 900 may represent the distal end of second longitudinal element 108 (referring to FIG. 1).

A pushing element 908 may be disposed within a lumen 910 defined by elongate member 902. Pushing element 908 may be coupled to actuator 140 in any suitable manner. Pushing element 908 may be advanced distally by actuator 140 and may contact a fiducial source 911 disposed within lumen 910. Fiducial source 911 may be a continuous length of fiducial material configured to be formed into a plurality of individual fiducials 912. Fiducials 912 may be substantially similar to fiducials 212 (referring to FIG. 2).

A separating mechanism 916 may be disposed at distal end 906 of medical device 900. Separating mechanism 916 may be substantially similar to separating mechanism 216 (referring to FIG. 2) and may be configured to form individual fiducials 912 from fiducial source 911, e.g., by the application of an electric charge, heat, or mechanical force. In one exemplary embodiment, as pushing element 908 is moved distally (e.g., by actuator 140 of FIG. 1), a distal end of fiducial source 911 may extend distally toward an opening 918 disposed at distal end 906 of elongate member 902. In an alternative embodiment, elongate member 902 may be moved proximally (while pushing member 908 is held in place) to direct a distal end of fiducial source 911 toward distal end 906.

In one embodiment, once fiducial source 911 has been distally advanced a sufficient amount, separating mechanism 916 may generate a separating force to form a distalmost fiducial 912. The distal advancement can be measured at the proximal end by movement of pushing member 908. In one embodiment, an actuator may also be a ratchet or other like mechanism at the proximal end to permit incremental advancement of pushing member 908. That is, in each increment, the actuator may move pushing member 908 a predetermined amount to deploy one or more fiducials 912. In one embodiment, separating mechanism 916 may emit an electrical charge that severs fiducial source 911 at a distal region to generate an individual fiducial 912. In an alternative embodiment, separating mechanism 916 may direct heat toward fiducial source 911, thereby generating and releasing a newly formed distalmost fiducial 912. It should be noted, however, that other alternative separating mechanisms utilizing electrical, mechanical, and/or chemical mechanisms are also contemplated.

FIGS. 10-11 are partial side cross-sectional views of a deployment mechanism in accordance with an embodiment of the present disclosure. A medical device 1000 may include an elongate member 1002 having a proximal end 1004 and a distal end 1006. Similar to elongate member 202, elongate member 1002 may be inserted into a lumen of a patient's body to access a target site whereupon a medical or diagnostic procedure, such as EUS FNA, is performed. The proximal end 1004 may be coupled to an actuating mechanism, such as actuator 140 (referring to FIG. 1), for operating the medical device 1000. In some embodiments, medical device 1000 may represent the distal end of second longitudinal element 108 (referring to FIG. 1).

A biasing element 1008 may be disposed within a lumen 1010 defined by elongate member 1002. Biasing element 1008 may be coupled to a plurality of stacked fiducials 1012 disposed within lumen 1010. A distal opening mechanism 1013 may include a cap 1014 coupled to an arm 1016 via a joint/pivot pin 1018. Fiducials 1012 may be substantially similar to fiducials 212 (referring to FIG. 2). In one embodiment, biasing element 1008 may be a coiled spring. Alternatively, biasing element 1008 may be any suitable structure capable of providing a biasing force including, but not limited to, other compressible materials.

To deploy a distalmost fiducial 1012, cap 1014 may be rotated about joint 1018 such that arm 1016 ejects the distalmost fiducial 1012 from lumen 1010 via an opening 1020. After a fiducial 1012 has been ejected, biasing element 1008 may urge a next distalmost fiducial 1012 to the distalmost position. Cap 1014 may be actuated at the proximal end via a pull wire (not shown) that couples cap 1013 to actuator 140 (referring to FIG. 1).

Figure 12:
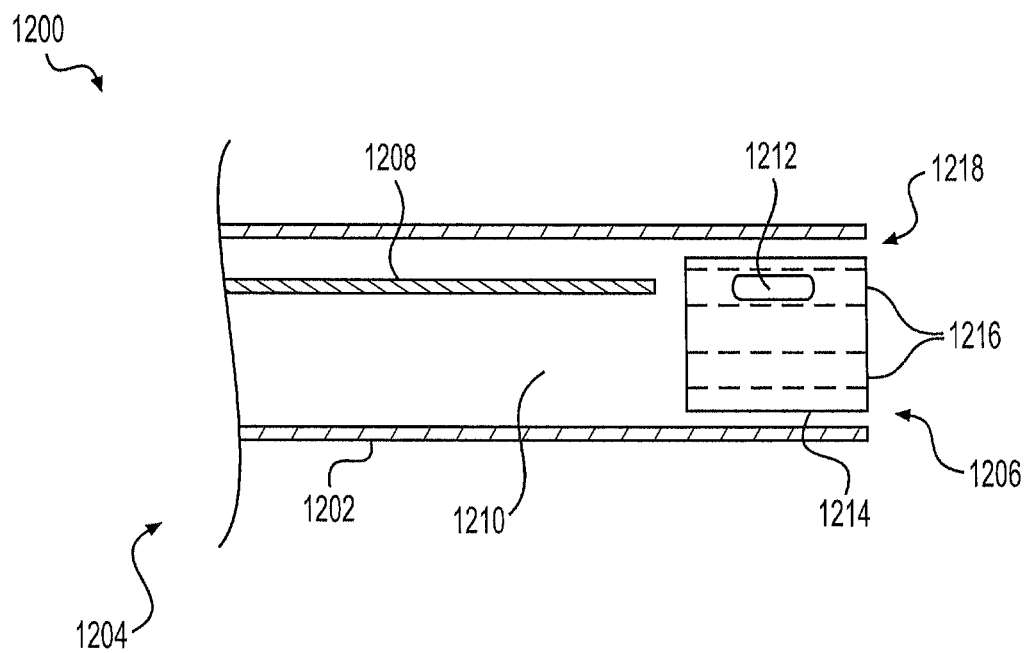
FIG. 12 is a partial side cross-sectional view of a deployment mechanism in accordance with an embodiment of the present disclosure.
Figure 13:
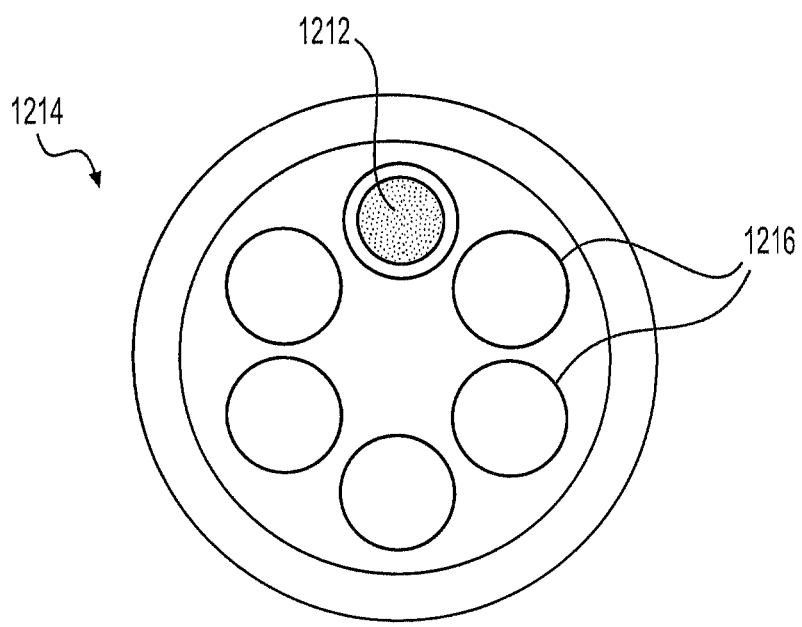
FIG. 13 is a top plan view of a cartridge used in conjunction with the deployment mechanism of FIG. 12.

FIGS. 12-13 depict a deployment mechanism in accordance with an embodiment of the present disclosure. A medical device 1200 may include an elongate member 1202 having a proximal end 1204 and a distal end 1206. Similar to elongate member 202, elongate member 1202 may be inserted into a lumen of a patient's body to access a target site whereupon a medical or diagnostic procedure, such as EUS FNA, is performed. The proximal end 1204 may be coupled to an actuating mechanism, such as actuator 140 (referring to FIG. 1), for operating the medical device 1200.

In some embodiments, medical device 1200 may represent the distal end of second longitudinal element 108 (referring to FIG. 1).

A pushing element 1208 may be disposed within a lumen 1210 defined by elongate member 1202. Pushing element 1208 may be coupled to actuator 140 in any suitable manner. Pushing element 1208 may be advanced distally by actuator 140 and may contact a fiducial 1212 disposed within a cartridge 1214. Cartridge 1214 may be disposed distal to pushing element 1208 within lumen 1210 and may be configured to hold fiducials 1212 in a plurality of chambers 1216 disposed in a radial arrangement about cartridge 1214. In one embodiment, cartridge 1214 may include six chambers 1216, though any other suitable number of chambers may be utilized, if desired. Fiducials 1212 may be substantially similar to fiducials 212 (referring to FIG. 2). Each fiducial 1212 may stay in a chamber 1216 via, e.g., a friction fit, until a sufficient force is applied by pushing member 1208.

In one exemplary embodiment, pushing element 1208 may be aligned with a first chamber 1216. As pushing element 1208 is moved distally through the first chamber 1216 (e.g., by actuator 140 of FIG. 1), a first fiducial 1212 disposed within first chamber 1216 may extend distally toward an opening 1218 disposed at distal end 1206 of elongate member 1202. In an alternative embodiment, cartridge 1214 may be moved proximally (while pushing member 1208 is held in place) to eject fiducials 1212 from chambers 1216.

Cartridge 1214 may then be rotated so that pushing element 1208 is aligned with a second chamber 1216. In an alternative embodiment, pushing element 1208 may be rotated to align with second chamber 1216.

In yet another alternative embodiment, a plurality of pushing elements 1208 may be aligned with an equal number of chambers 1216, such that each pushing element 1208 is aligned with a corresponding chamber 1216. In this embodiment, each pushing element 1208 may be aligned with a corresponding actuating mechanism.

Figure 14:
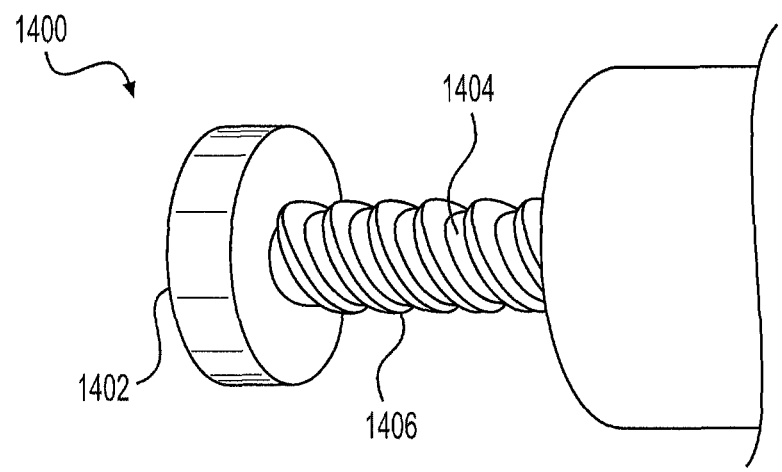
FIGS. 14-15 are partial side perspective views of exemplary actuators in accordance with various embodiments of the present disclosure.

FIG. 14 depicts an actuating mechanism in accordance with an embodiment of the present disclosure. Medical device 1400 may include a proximal cap 1402, an elongate member 1404, and a plurality of threads 1406 disposed along the length of elongate member 1404. This particular embodiment may allow for precision in the deployment of fiducials in accordance with other embodiments of the present disclosure. In some embodiments, the length and geometry of threads 1406 may be configured such that, e.g., one full rotation of proximal cap 1402 may deploy one fiducial from a distal end of a medical device. In some embodiments, medical device 1400 may represent actuator 140 of FIG. 1. In some embodiments, proximal cap 1402 may be moved distally to deploy fiducials into a patient's body, while in other embodiments, proximal cap 1402 may be moved proximally to deploy the fiducials.

Figure 15:
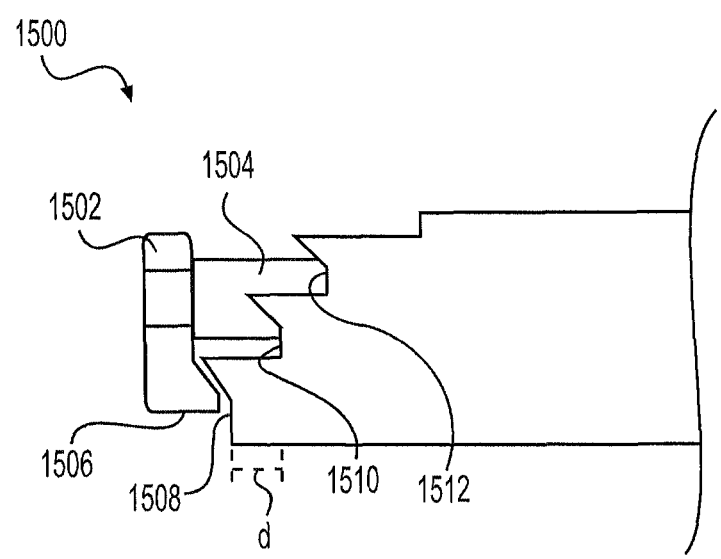

FIG. 15 depicts an actuating mechanism in accordance with an embodiment of the present disclosure. Medical device 1500 may include a proximal cap 1502, an elongate member 1504, and a protrusion 1506 extending distally from proximal cap 1502. Medical device 1500 may also include a plurality of seats configured to cooperate with protrusion 1506. This particular embodiment may also allow for precision in the deployment of fiducials in accordance with other embodiments of the present disclosure. In one embodiment, medical device 1500 includes three seats 1508, 1510, and 1512. In some embodiments, a distally adjacent seat may be transposed about the longitudinal axis of medical device 1500 with respect to a proximally adjacent seat. For example, seat 1510 may be distal to seat 1508 and may be transposed about the longitudinal axis of medical device 1500 in either a clockwise or counterclockwise direction. To deploy a first fiducial (not shown in FIG. 15), a user may rotate cap 1502 so that protrusion 1506 is aligned with seat 1510, and then apply a distal force to cap 1502 so that protrusion 1506 and seat 1510 contact each other or are otherwise coupled. The distance d traveled by protrusion 1506 may be configured to deploy a precise number of fiducials (e.g., one fiducial). In some embodiments, medical device 1500 may represent actuator 140 of FIG. 1. To deploy a second fiducial (not shown in FIG. 15), the user may rotate cap 1502 so that protrusion 1506 is aligned with seat 1512, and then apply a distal force to cap 1502 so that protrusion 1506 and seat 1512 are coupled. While three seats are depicted in the embodiment of FIG. 15, any suitable number of seats may alternatively be utilized.

Any aspect set forth in any embodiment may be used with any other embodiment set forth herein. Every device and apparatus set forth herein may be used in any suitable medical procedure, may be advanced through any suitable body lumen and body cavity, and may be used to access tissue from any suitable body portion. For example, the apparatuses and methods described herein may be used through any natural body lumen or tract, including those accessed orally, vaginally, rectally, nasally, urethrally, or through incisions in any suitable tissue.

It will be apparent to those skilled in the art that various modifications and variations can be made in the disclosed systems and processes without departing from the scope of the invention. Other embodiments of the disclosure will be apparent to those skilled in the art from consideration of the specification and practice of the disclosure disclosed herein. It is intended that the specification and examples be considered as exemplary only. The following disclosure identifies some other exemplary embodiments.

We claim:

1. A medical device, comprising:
   a member having a proximal end and a distal end;
   a lumen disposed through the member;
   an opening disposed at the distal end of the member in communication with the lumen;
   an element disposed with the lumen;
   a plurality of fiducials disposed within the lumen and distal to the element, wherein adjacent fiducials of the plurality of fiducials are disposed within compartments separated by spacers; and
   a separating mechanism disposed at the distal end of the member, the separating mechanism configured to apply a separating force to deploy one fiducial of the plurality of fiducials as other fiducials of the plurality of fiducials remain disposed within the lumen, wherein the separating mechanism is configured to apply the separating force to a distalmost spacer to deploy a distalmost fiducial, and;
   the separating mechanism is configured to emit an electrical charge to sever the distalmost spacer to deploy the distalmost fiducial, is configured to direct heat toward the distalmost spacer to deploy the distalmost fiducial, or is a chemical separating mechanism.

2. The medical device of claim 1, wherein each compartment is enclosed by a different combination of exactly two spacers.

3. The medical device of claim 2, including at least three compartments.

4. The medical device of claim 3, wherein each of the spacers is movable relative to the distal end of the member.

5. A method of deploying one or more fiducials within a patient, the method comprising:
   advancing a medical device into a body lumen of the patient, wherein the medical device includes a lumen having a plurality of compartments, wherein each of the compartments is enclosed by a different combination of two spacers, and each compartment contains a fiducial;
   applying a distally-directed force to direct at least one fiducial toward an opening at a distal end of the medical device; and
   applying a separating force, distinct from the distally-directed force, to deploy the fiducial, wherein the separating force is an electric charge or heat.

6. The method of claim 5, wherein the distally-directed force is applied by an element disposed within the lumen of the medical device.

7. The method of claim 5, wherein each compartment includes exactly one fiducial.

8. The method of claim 5, wherein the distally-directed force is applied to a proximalmost spacer.

9. The method of claim 8, wherein, when the distally-directed force is applied to the proximalmost spacer, each spacer and each fiducial is moved distally through the lumen of the medical device.

10. A medical device, comprising:
    a member having a proximal end and a distal end;
    a first lumen disposed through the member;
    an opening disposed at the distal end of the member in communication with the first lumen;
    a plurality of fiducials disposed within the first lumen;
    at least one biasing element disposed within the first lumen proximal to the plurality of fiducials, the at least one biasing element configured to urge the plurality of fiducials toward the opening after deployment of a distalmost fiducial;
    a second lumen disposed in the member and parallel to the first lumen, wherein a central longitudinal axis of the first lumen is radially offset from a central longitudinal axis of the second lumen; and
    a pushing element disposed through the second lumen, the pushing element being configured to reciprocally move between a proximal loading position and a distal deployment position, wherein when the pushing element is in the proximal loading position and no fiducial is in the second lumen, a distalmost fiducial disposed within the first lumen is urged laterally toward the second lumen by the at least one biasing element.

11. The medical device of claim 10, wherein the pushing element is disposed in the second lumen and not in the first lumen.

12. The medical device of claim 11, wherein the at least one biasing element is a spring disposed in the first lumen and not in the second lumen.

13. The medical device of claim 12, further including a tapered wall at the distal end of the member, wherein the distalmost fiducial is guided from the first lumen laterally toward the second lumen by the tapered wall.

14. The medical device of claim 13, further including a separating wall disposed within the member that radially separates the first lumen from the second lumen along an entire length of the separating wall.

* * * * *